(12) United States Patent
Smith et al.

(10) Patent No.: US 10,537,378 B2
(45) Date of Patent: Jan. 21, 2020

(54) VARIABLE ACTIVE CLIPPER CIRCUIT TO CONTROL CREST FACTOR IN AN AC POWER CONVERTER

(71) Applicant: COVIDIEN LP, Mansfield, MA (US)

(72) Inventors: Robert B. Smith, Loveland, CO (US); Steven C. Rupp, Arvada, CO (US); Daniel A. Friedrichs, Aurora, CO (US)

(73) Assignee: Covidien LP, Mansfield, MA (US)

( * ) Notice: Subject to any disclaimer, the term of this patent is extended or adjusted under 35 U.S.C. 154(b) by 687 days.

(21) Appl. No.: 15/062,460

(22) Filed: Mar. 7, 2016

(65) Prior Publication Data

US 2017/0252090 A1 Sep. 7, 2017

(51) Int. Cl.
*A61B 18/12* (2006.01)
*A61B 18/00* (2006.01)

(52) U.S. Cl.
CPC ...... *A61B 18/1233* (2013.01); *A61B 18/1206* (2013.01); *A61B 2018/0072* (2013.01); *A61B 2018/00678* (2013.01); *A61B 2018/1266* (2013.01)

(58) Field of Classification Search
CPC .......... A61B 18/1233; A61B 18/10; A61B 2018/00636–00904; A61B 18/1206–1293; H03G 11/02; H03F 2201/3236; H04L 27/2623
See application file for complete search history.

(56) References Cited

U.S. PATENT DOCUMENTS

| | | | | |
|---|---|---|---|---|
| 5,472,443 A * | 12/1995 | Cordis | .................. | A61B 18/12 606/32 |
| 7,199,633 B2 | 4/2007 | Gerding et al. | | |
| 2005/0162095 A1* | 7/2005 | Kendrick | ............. | H05B 39/044 315/247 |
| 2007/0038209 A1 | 2/2007 | Buysse et al. | | |
| 2009/0108815 A1* | 4/2009 | Overland | ............. | H02M 7/217 320/166 |
| 2012/0150170 A1 | 6/2012 | Buysse et al. | | |
| 2013/0208515 A1* | 8/2013 | Swamy | .................. | H02M 1/36 363/37 |
| 2015/0025523 A1* | 1/2015 | Friedrichs | .......... | A61B 18/1206 606/34 |

* cited by examiner

*Primary Examiner* — Eun Hwa Kim
*Assistant Examiner* — Catherine Premraj (57) ABSTRACT

An electrosurgical generator includes: a power supply configured to output a DC waveform; a current or voltage source coupled to the power supply and configured to output current; and a power converter coupled to the current source. The power converter includes at least one power switching element operated at a switching waveform and configured to generate a radio frequency waveform based on the energy from the current or voltage source. The radio frequency waveform includes at least one pulse having an overshoot peak. The electrosurgical generator further includes a clipper circuit coupled to the current source and the power converter, the clipper circuit configured to generate a clipping voltage to clip the overshoot peak; and a controller coupled to the power converter and configured to modulate the switching waveform to generate the radio frequency waveform.

18 Claims, 5 Drawing Sheets

VARIABLE ACTIVE CLIPPER CIRCUIT TO CONTROL CREST FACTOR IN AN AC POWER CONVERTER

BACKGROUND

Technical Field

The present disclosure relates to systems and methods for controlling an electrosurgical generator. In particular, the present disclosure relates to an electrosurgical generator including an active clipper circuit for controlling a crest factor of a radio frequency waveform generated by a power converter.

Background of Related Art

Electrosurgery involves application of electrical energy to a surgical site to cut, ablate, desiccate, or coagulate tissue. In monopolar electrosurgery, a source or active electrode delivers electrical current from an electrosurgical generator to targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Conventional electrosurgical generators rely on output filtering to shape the waveform of the power output by the generator. Electrosurgical generators may include alternating current ("AC") power converters, which generate substantially sinusoidal waveforms at predetermined frequencies. In conventional electrosurgical generators, it is known to adjust a crest factor of an electrosurgical waveform to control tissue effect. Crest factor is a ratio of peak voltage value to root mean square ("RMS") value of the waveform. Thus, for example, a pure square waveform has a crest factor of about 1 and a pure sinusoidal waveform has a crest factor of about 1.414, since the peak of a true sinusoid is 1.414 times its RMS value.

Conventional electrosurgical generators may also include resonant output filters to produce sine wave waveforms from RF converters. Thus, these generators operate at a single frequency and rely on the filtering to remove unwanted harmonics. The crest factor of a filtered output may be changed using time domain manipulation such as duty cycle modulation (e.g., by sending out a short burst of pulses). However, there are several drawbacks and limitations to the performance of the conventional resonant devices. Crest factor control is significantly limited by characteristics of the hardware filters since these filters only work over a very limited frequency range or a fixed frequency and crest factor changes dramatically for a given duty cycle with variations in load impedance. Duty cycle modulation produces many subharmonic frequencies, which can contribute to electromuscular stimulation. Furthermore, crest factors below 1.4 are not achievable using generators including resonant networks.

Accordingly, there is a need for new and improved systems and method for controlling electrosurgical generators, which are not limited to any particular narrow frequency range and do not require output filtering to achieve reasonable power output.

SUMMARY

The present disclosure provides for an electrosurgical generator including a power converter having a plurality of switching elements, such as FETs. The generator also includes a current or voltage source, which may be an inductor. The current or voltage source supplies current or voltage to the power converter. A variable active clipper circuit mitigates some of the effects of the current or voltage source on the power converter to achieve desired crest factor control.

Electrosurgical generators according to the present disclosure may include voltage-fed converters, which operate based on switching on/off of switching-elements to control the power. Electrosurgical generators according to the present disclosure may also include current-fed converters, which control power delivery by shorting the current to ground, or some other return path. Thus, when the voltage-fed converter turns on all of the switching elements, this results in large power dissipation with destructive currents. To deal which these surges, at least one of the switching elements may advantageously be open or off at all times. For the current-fed converter, shorting or shunting the current source, e.g., an inductor, no significant power is dissipated while the current flow is maintained.

The generator according to the present disclosure may include non-resonant architecture and hence, may not require tuned output filtering. The generator may include a power converter which is input power limited. The generator according to the present disclosure may also include either a current-fed or voltage-fed topology and a current source (e.g., an inductance) coupled to the power converter.

According to one embodiment of the present disclosure, an electrosurgical generator is described. The electrosurgical generator includes: a power supply configured to output a DC waveform; a current source coupled to the power supply and configured to output current; and a power converter coupled to the current source. The power converter includes at least one power switching element operated at a switching waveform and configured to generate a radio frequency waveform based on the current from the current source. The radio frequency waveform includes at least one pulse having an overshoot peak. The electrosurgical generator further includes a clipper circuit coupled to the current source and the power converter. The clipper circuit is configured to generate a clipping voltage to clip the overshoot peak. The electrosurgical generator also includes a controller coupled to the power converter and configured to modulate the switching waveform to generate the radio frequency waveform.

According to another embodiment of the present disclosure, an electrosurgical generator is described. The electrosurgical generator include: a power supply configured to output a DC waveform; a voltage source coupled to the power supply and configured to output a voltage; and a power converter coupled to the voltage source. The power converter includes at least one power switching element operated at a switching waveform and configured to generate a radio frequency waveform based on the voltage from the voltage source. The radio frequency waveform includes at least one pulse having an overshoot peak. The electrosurgical generator further includes a clipper circuit coupled to the current source and the power converter. The clipper circuit is configured to generate a clipping voltage to clip the overshoot peak. The electrosurgical generator also includes a controller coupled to the power converter and configured to modulate the switching waveform to generate the radio frequency waveform.

According to one aspect of any of the above embodiments, the power converter includes four power switching elements arranged in an H-bridge topology.

According to another aspect of any of the above embodiments, the clipper circuit may include a clipper inductor, a clipper capacitor, and a clipper catch diode, all of which are interconnected in series. The clipper circuit may further include at least one clipper switching element coupling the clipper inductor to the clipper capacitor and the clipper catch diode. The controller is coupled to the clipper circuit and is configured to control the at least one clipper switching element to maintain the clipping voltage at the clipper capacitor.

According to a further aspect of any of the above embodiments, the clipping voltage is substantially equal to a root mean square voltage of the radio frequency waveform.

According to a further embodiment of the present disclosure, a method for controlling an electrosurgical generator is described. The method includes: activating a first pair of power switching elements and a second pair of power switching elements of a power converter; deactivating the first pair of the power switching elements to generate a radio frequency waveform including at least one pulse having an overshoot peak; and activating a clipper circuit coupled to the power converter to generate a clipping voltage to clip the overshoot peak.

According to one aspect of the above embodiment, the method further includes deactivating at least one power switching element of the second pair of the power switching elements.

According to another aspect of the above embodiment, activating the clipper circuit includes: increasing voltage at a clipper inductor of the clipper circuit, clamping current at the clipper inductor by a clipper catch diode of the clipper circuit, charging a clipper capacitor of the clipper circuit, and controlling at least one clipper switching element of the clipper circuit to maintain the clipping voltage at the clipper capacitor.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

A generator may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
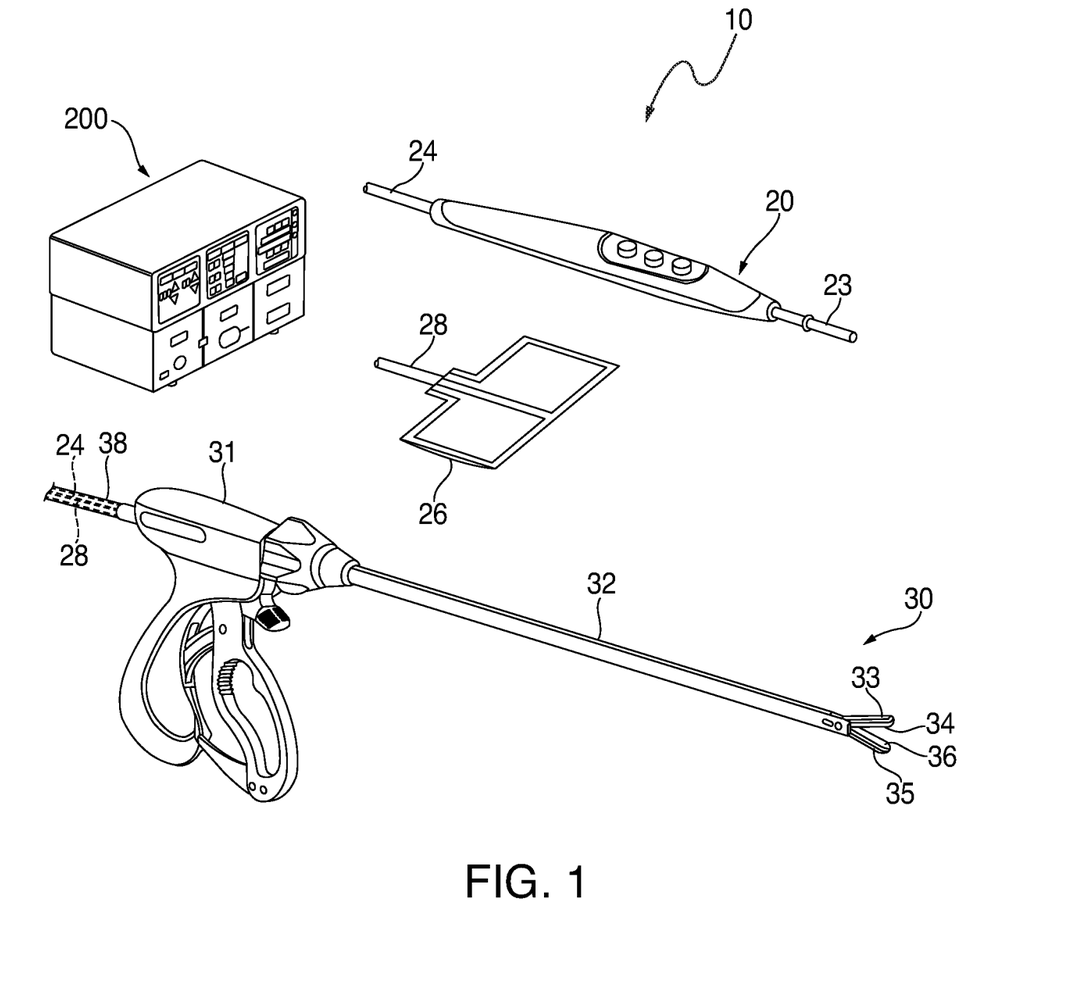
FIG. 1 is a perspective view of a surgical system according to an embodiment of the present disclosure.

FIG. 1 is a perspective view of the components of one illustrative embodiment of an electrosurgical system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 230 (FIG. 3) of the generator 200, allowing the instrument 20 to cut, coagulate, thermally or non-thermally ablate and/or otherwise treat tissue. The alternating current is returned to the generator 200 through a return electrode pad 26 via a return line 28 at a return terminal 232 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
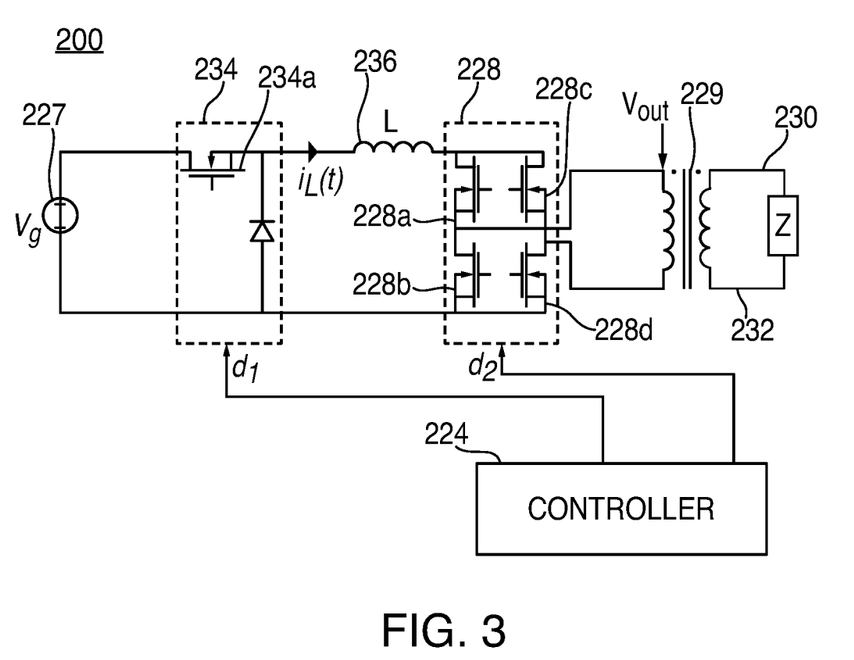
FIG. 3 is a schematic diagram of the electrosurgical generator of FIG. 2 according to an embodiment of the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 230, 232, respectively (FIG. 3). The electrosurgical forceps 30 is coupled to the generator 200 at a port having connections to the active and return terminals 230 and 232 (e.g., pins) via a plug disposed at the end of the cable 38, wherein the plug includes contacts from the supply and return lines 24, 28 as described in more detail below.

Figure 2:
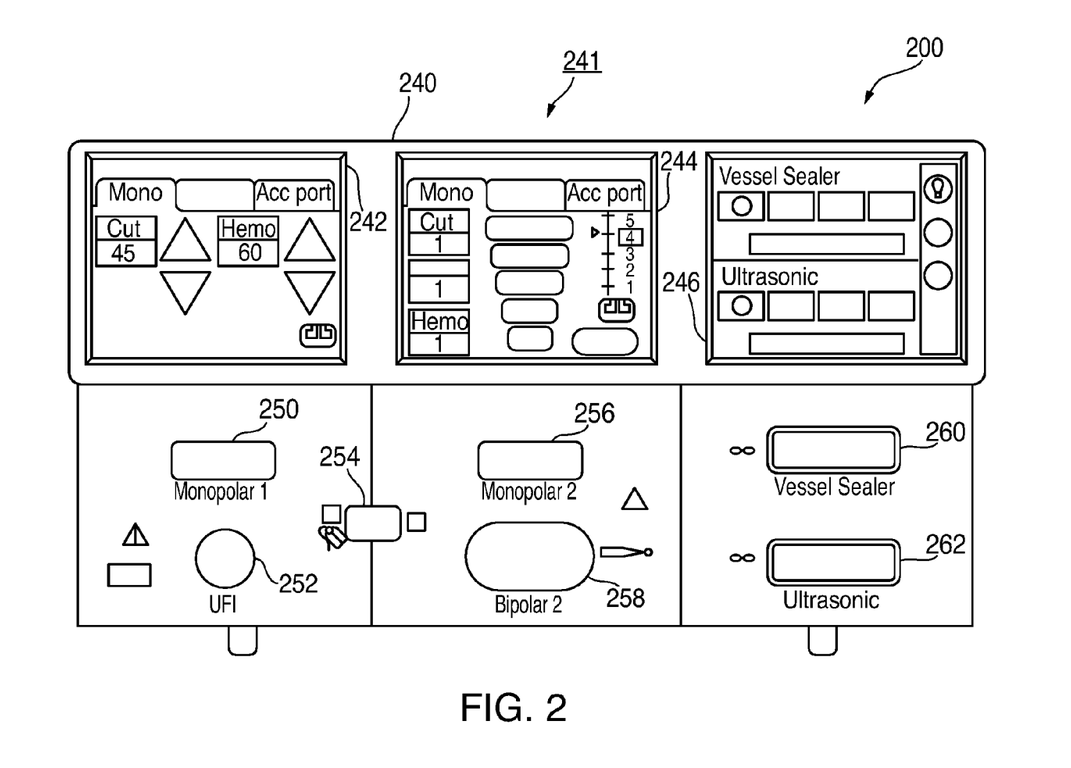
FIG. 2 is a front view of an electrosurgical generator of FIG. 1 according to an embodiment of the present disclosure.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a one or more of ports 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). The port 254 is configured to couple to the return electrode pad 26. Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 that may be plugged into one of the ports 260 and 262. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 224 (FIG. 3) where the setting may be saved in memory. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals 230 and 232 may be coupled to any of the desired ports 250-262. In embodiments, the active and return terminals 230 and 232 may be coupled to the ports 250-262.

FIG. 3 shows a schematic block diagram of the generator 200, which includes a controller 224, a power supply 227, and a power converter 228. The power supply 227 may be a high voltage, DC power supply connected to an AC source (e.g., line voltage) and provides high voltage, DC power to the power converter 228, which then converts high voltage, DC power into RF energy and delivers the energy to the active terminal 230. The energy is returned to the power converter 228 via the return terminal 232. In particular, electrosurgical energy for energizing the monopolar electrosurgical instrument 20 and/or electrosurgical forceps 30 is delivered through the active and return terminals 230 and 232. The active and return terminals 230 and 232 are coupled to the power converter 228 through an isolation transformer 229.

The generator 200 also includes a DC-DC buck converter 234 coupled to the power supply 227. The generator 200 includes a current source 236 is electrically coupled to the DC-DC buck converter 234 and the power converter 228. The current source 236 may be an inductor having a relatively large inductance which smoothes the current supplied to the power converter 228. The current source 236 is configured to supply relatively constant current to the power converter 228. The output of power converter 228 transmits current through an isolation transformer 229 to the load "Z", e.g., tissue being treated.

The power converter 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 228 is a non-resonant RF amplifier. A non-resonant RF amplifier, as used herein, denotes an amplifier lacking any tuning components, e.g., conductors, capacitors, etc., disposed between the power converter and the load "Z." A non-resonant RF amplifier, such as the power converter 228, overcomes the limitations of resonant RF amplifiers as it is not limited to any particular narrow frequency ranges as required by the tuning components.

The controller 224 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that any logic processor (e.g., control circuit) adapted to perform the calculations and/or set of instructions described herein may be substituted for the processor.

The controller 224 includes an output port that is operably connected to the power supply 227 and/or power converter 228 allowing the processor to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or power converter 228, which adjusts the DC and/or power supply, respectively.

The generator 200 according to the present disclosure may also include a plurality of sensors (not shown). The sensors may be coupled to the power supply 227, the current source 234, and/or power converter 228 and may be configured to sense properties of DC current supplied to the power converter 228 and/or RF energy outputted by the power converter 228. Various components of the generator 200, namely, the power converter 228, the current and voltage sensors, may be disposed on a printed circuit board (PCB). The controller 224 also receives input signals from the input controls of the generator 200, the instrument 20 and/or electrosurgical forceps 30. The controller 224 utilizes the input signals to adjust power outputted by the generator 200 and/or performs other control functions thereon.

The DC-DC buck converter 234 includes a switching element 234a and power converter 228 includes a plurality of switching elements 228a-228d arranged in an H-bridge topology. In embodiments, power converter 228 may be configured according to any suitable topology including, but not limited to, half-bridge, full-bridge, push-pull, and the like. Suitable switching elements include voltage-controlled devices such as transistors, field-effect transistors (FETs), combinations thereof, and the like.

The controller 224 is in communication with both DC-DC buck converter 234 and power converter 228, in particular, the switching elements 234a and 228a-228d, respectively. Controller 224 is configured to output control signals, which may be a pulse-width modulated signal, to switching elements 234a and 228a-228d as described in further detail in US Publication No. US 2014/0254221, the entire contents of which are incorporated by reference herein. In particular, controller 224 is configured to modulate a control signal $d_1$ supplied to switching element 234a of DC-DC buck converter 234 and control signals $d_2$ supplied to switching elements 228a-228d of power converter 228. The control signal $d_1$ is a pulse-width modulated signal and adjusts the duty cycle of the switching elements 228a-228d to provide crest factor control.

Additionally, controller 224 is configured to measure power characteristics of generator 200, and control generator 200 based at least in part on the measured power characteristics. Examples of the measured power characteristics include the current through inductor 103 and the voltage at the output of power converter 228.

Figure 4:
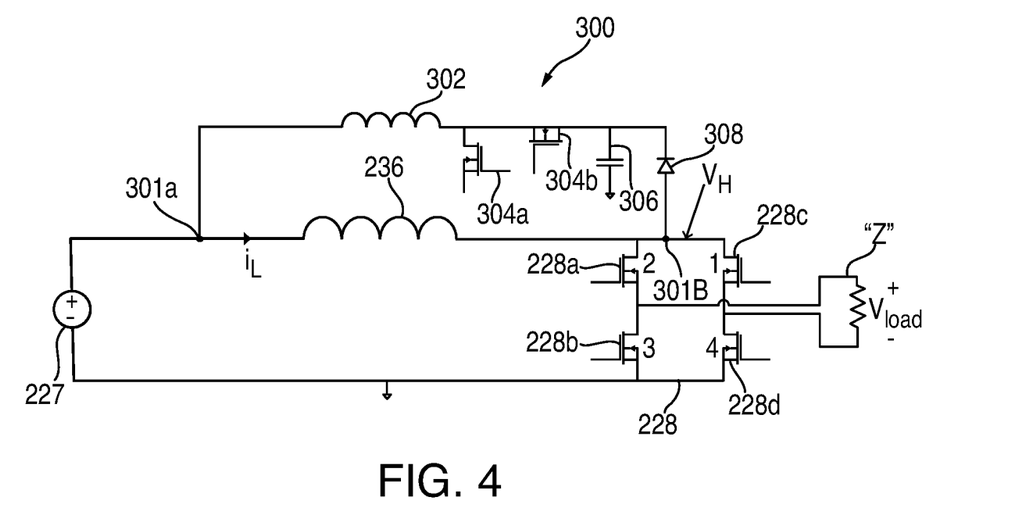
FIG. 4 is a schematic diagram of another embodiment of the electrosurgical generator of FIG. 2 according to the present disclosure.

As noted above, the power converter 228 may be current-fed or voltage-fed. To avoid unnecessary repetition only a current-fed embodiment of the generator 200 is described in detail below with respect to FIGS. 4-7, however, this configuration may also be applied to a voltage-fed power converter. With reference to FIG. 4, the power converter 228 of the generator 200 is shown as a current-source power converter coupled to a variable active clipping circuit 300. The clipping circuit 300 is configured to control the crest factor of the waveform generated by the power converter 228 by limiting or clipping of the edges of the pulses of the output RF waveform with a soft voltage controlled limiter. This configuration provides a more versatile and accurate crest factor control regardless of load impedance. In embodiments, the PWM control of the power converter 228 described above through the control signal $d_1$ may be combined with the clipping of the clipping circuit 300 to achieve a desired crest factor control.

The clipping circuit 300 is coupled in parallel to the current source 236. The clipping circuit 300 includes a first node 301a disposed between the power supply 227 and the current source 236 and a second node 301b coupled to the power converter 228. The clipping circuit 300 includes a clipping inductor 302, a first switching element 304a, and a second switching element 304b. The first switching element 304a is connected to a ground (not shown) and the second switching element 304b is connected in series to the power converter 228. The clipping circuit 300 also includes a clipping capacitor 306 and a clipping catch diode 308. The first and second switching elements 304a and 304b are configured to be switched at a fixed duty cycle by the controller 204 to establish the desired voltage at the clipping capacitor 306. The voltage in the clipping capacitor 306 is constantly being controlled via the first and second switching elements 304a and 304b and the clipping inductor 302 to maintain the desired capacitor voltage. Duty cycle is varied by a conventional buck/boost converter as required to obtain the desired crest factor.

In embodiments, the clipping circuit 300 may include a single switching element, such as the second switching element 304b. In this embodiment, the switching element 304a is replaced by a diode such that large voltages generated by the inductor 302 when the switching 304b is turned off.

The clipping circuit 300 is configured to output a clipping voltage back to the current source 236, which clips and/or limits the peak voltage of an RF waveform output by the power converter 228. More specifically, the clipping voltage may be set above the RMS voltage of the RF waveform to increase the crest factor of the RF waveform, whereas decreasing the clipping voltage relative to the RMS voltage reduces the crest factor. In embodiments, the clipping voltage may be set to be substantially equal to the RMS voltage of the RF waveform. The clipping voltage is controlled by the first and second switching elements 304a and 304b, which are controlled by the controller 204. The clipping voltage may be controlled automatically based on a desired crest factor. The crest factor may be also selected automatically based on the selected RF waveform. In embodiments, the crest factor may be selected by the user. In either embodiment, once the crest factor is selected, the controller 204 toggles the first and second switching elements 304a and 304b to maintain the clipping voltage to achieve the desired crest factor as described in more detail below.

Figure 5:
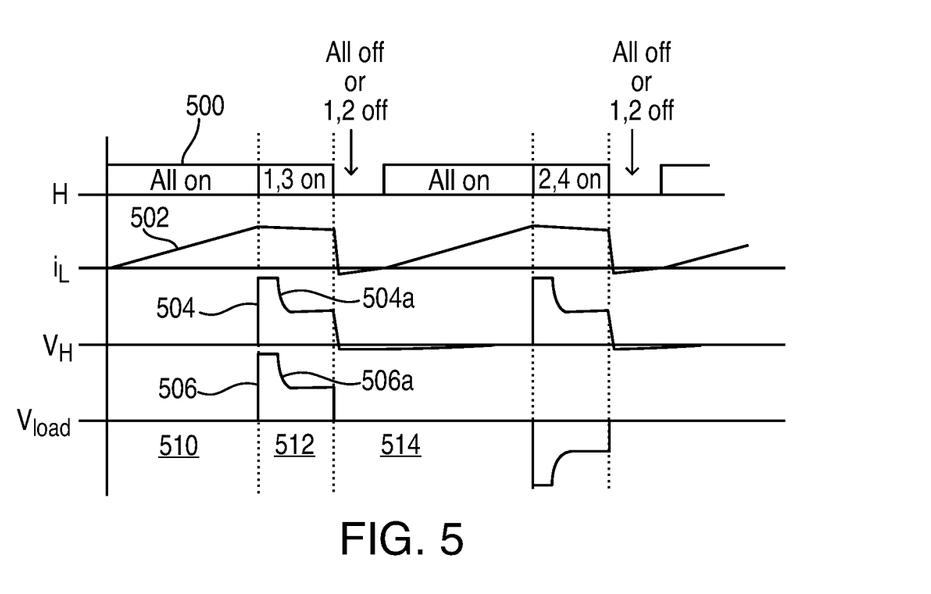
FIG. 5 is a plot of a switching waveform, a generator output waveform, a power converter waveform, and a current source waveform for generating a high crest factor waveform according to the present disclosure.

FIG. 5 illustrates a plurality of waveforms for generating a high crest factor RF waveform 506, namely, a pulse width modulated ("PWM") switching waveform 500 (e.g., control signal $d_1$) for switching the switching elements 228a-228d, a waveform 502 generated by the current source 236, and a converted waveform 504 generated by the power converter 228.

Initially, during period 510 as shown in FIG. 5, all of the switching elements are turned on by the switching waveform 500 and current in the current source 236 ramps up to a desired predetermined level. Once the desired current is achieved, which may be determined by sensors (not shown) coupled to the controller 224, one pair of the switching elements 228a-228d, e.g., switching element 228a, and 228d or 228b and 228c, are turned off.

The timing for turning off a pair of switching elements 228a-228d depends on the desired crest factor and is controlled by the switching waveform 500. This generates a first RF pulse (e.g., positive half cycle) that is supplied to the load "Z" during period 512. Voltage at power converter 228 and the load "Z" initially overshoots as demonstrated by overshoot peaks 504a and 506a, respectively, of the pulses in each of the waveforms 504 and 506. The overshoot is due to the current built up in the current source 236.

The clipping circuit 300 clips the voltage overshoot and diverts the clipped current into the clipping capacitor 306 and back to the current source 236. In particular, the voltage at the output of the clipping inductor 302 rises very rapidly and is clamped by the clipping catch diode 308, which then feeds the energy into the clipping capacitor 306. As a result, the voltage of the pulses levels off to a stable level until the end of the pulses. More specifically, the power supply 227 feeding the current source 236 is turned off, ending the pulses of the waveforms 504 and 506.

At a predetermined time, during period 514, one of the high side switching elements, namely, switching element 228a, or 228b, of the pair of the switching elements 228a and 228d or 228b and 228c, may also tuned off. As a result, all but one of the switching elements 228a-228d is turned off, namely, one of the low side switching elements 228c or 228d remains on. In embodiments, all of the remaining activated switching elements may also be turned off.

Thereafter, all of the switching element 228a-228d turn on to start the next cycle, which results in a reverse RF pulse (e.g., negative half cycle of the waveform 506) as compared to the pulse generated previously during period 512. The application of switching waveform 500 is repeated indefinitely to generate the desired waveform 506. In this embodiment, the PWM pulses of the switching waveform 500 are relatively short as compared to the pulses of a switching waveform 600 for generating a low crest factor waveform 606 as described in more detail below with respect to FIG. 6. The clipping voltage at the clipper circuit 300 is increased to allow more overshoot before the output of the waveforms 504 and 506 is stabilized at each pulse.

Figure 6:
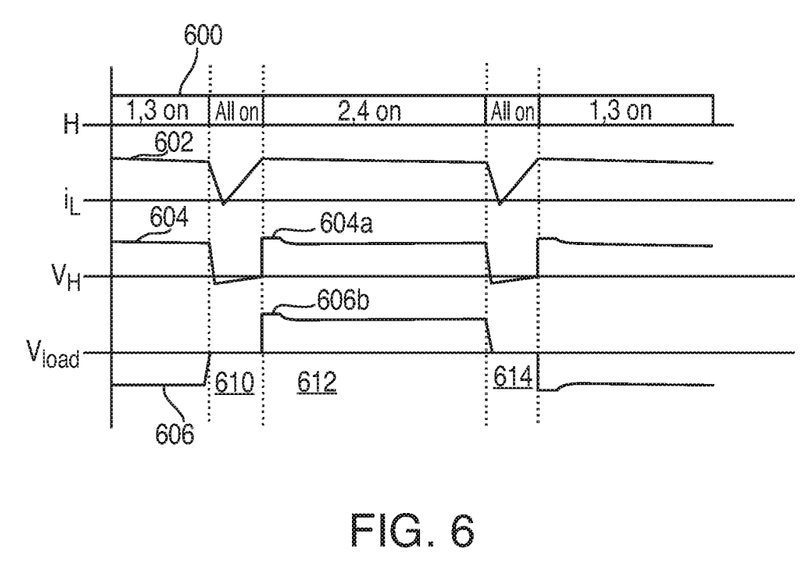
FIG. 6 is a plot of a switching waveform, a generator output waveform, a power converter waveform, and a current source waveform for generating a low crest factor waveform according to the present disclosure.

FIG. 6 illustrates a plurality of waveforms for generating a low crest factor RF waveform 606, namely, a switching waveform 600 (e.g., control signal $d_1$) for switching the switching elements 228a-228d, a waveform 602 generated by the current source 236, and a converted waveform 604 generated by the power converter 228.

Initially, during period 610 as shown in FIG. 6, all of the switching elements are turned on by the switching waveform 600 and current in the current source 236 drops initially and then ramps up to a desired predetermined level. Once the desired current is achieved, which may be determined by sensors (not shown) coupled to the controller 224, one pair of the switching elements 228a-228d, e.g., switching element 228a, and 228d or 228b and 228c, are turned off. This generates a first RF pulse (e.g., positive half cycle) that is supplied to the load "Z" during period 612.

The timing for turning off a pair of switching elements 228a-228d depends on the desired crest factor and is controlled by the switching waveform 600. Voltage at power converter 228 and the load "Z" initially overshoots as demonstrated by peaks 604a and 606a of the pulses in each of the waveforms 604 and 606, respectively. The overshoot is due to the current built up in the current source 236. However, the overshoot for pulses the low crest factor waveform 606 is much smaller than the overshoot of the pulses of the high crest factor waveform 506 seen in FIG. 5.

The clipping circuit 300 clips the voltage overshoot and diverts the clipped current into the clipping capacitor 306 and back to the current source 236. In particular, the voltage at the output of the clipping inductor 302 rises very rapidly and is clamped by the clipping catch diode 308, which then feeds the energy into the clipping capacitor 306. As a result, the voltage of the pulses levels off to a stable level until the end of the pulses. More specifically, the power supply 227 feeding the current source 236 is turned off, ending the pulses of the waveforms 604 and 606.

Thereafter, during period 614, all of the switching element 228a-228d turn on to start the next cycle, which results in a reverse RF pulse (e.g., negative half cycle of the waveform 606) as compared to the pulse generated previously during period 612. The application of switching waveform 600 is repeated indefinitely to generate the desired waveform 606. As a result, an almost pure square wave is produced having approximately 100% duty cycle. In this embodiment, the clipping voltage of the clipper circuit 300 is set to be substantially equal to the desired output voltage of the waveform 606. The inherent ringing of the output network is clipped by the clipping circuit 300 and the crest factor at the load remains very nearly at unity.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical generator, comprising:
   a power supply configured to output a direct current (DC) waveform;
   a current source coupled to the power supply and configured to output current;
   a power converter coupled to the current source, the power converter including at least one power switching element operated at a switching waveform and configured to generate a radio frequency waveform based on the current from the current source, the radio frequency waveform including at least one pulse having an overshoot peak;
   a clipper circuit coupled to the current source and the power converter, the clipper circuit configured to generate a clipping voltage to clip the overshoot peak; and
   a controller coupled to the power converter and configured to modulate the switching waveform to generate the radio frequency waveform.

2. The electrosurgical generator according to claim 1, wherein the power converter includes four power switching elements arranged in an H-bridge topology.

3. The electrosurgical generator according to claim 1, wherein the clipper circuit includes a clipper inductor, a clipper capacitor, and a clipper catch diode, all of which are interconnected in series.

4. The electrosurgical generator according to claim 3, wherein the clipper circuit further includes at least one clipper switching element coupling the clipper inductor to the clipper capacitor and the clipper catch diode.

5. The electrosurgical generator according to claim 4, wherein the controller is coupled to the clipper circuit and is configured to control the at least one clipper switching element to maintain the clipping voltage at the clipper capacitor.

6. The electrosurgical generator according to claim 1, wherein the clipping voltage is substantially equal to a root mean square voltage of the radio frequency waveform.

7. An electrosurgical generator, comprising:
   a power supply configured to output a direct current (DC) waveform;
   a voltage source coupled to the power supply and configured to output a voltage;
   a power converter coupled to the voltage source, the power converter including at least one power switching element operated at a switching waveform and configured to generate a radio frequency waveform based on the voltage from the voltage source, the radio frequency waveform including at least one pulse having an overshoot peak;
   a clipper circuit coupled to the voltage source and the power converter, the clipper circuit configured to generate a clipping voltage to clip the overshoot peak; and a controller coupled to the power converter and configured to modulate the switching waveform to generate the radio frequency waveform.

8. The electrosurgical generator according to claim 7, wherein the power converter includes four power switching elements arranged in an H-bridge topology.

9. The electrosurgical generator according to claim 7, wherein the clipper circuit includes a clipper inductor, a clipper capacitor, and a clipper catch diode, all of which are interconnected in series.

10. The electrosurgical generator according to claim 9, wherein the clipper circuit further includes at least one clipper switching element coupling the clipper inductor to the clipper capacitor and the clipper catch diode.

11. The electrosurgical generator according to claim 10, wherein the controller is coupled to the clipper circuit and is configured to control the at least one clipper switching element to maintain the clipping voltage at the clipper capacitor.

12. The electrosurgical generator according to claim 7, wherein the clipping voltage is substantially equal to a root mean square voltage of the radio frequency waveform.

13. A method for controlling an electrosurgical generator, the method comprising:
   activating a first pair of power switching elements and a second pair of power switching elements of a power converter, wherein the power converter is disposed within the electrosurgical generator, the electrosurgical generator including a power supply configured to output a direct current (DC) waveform;
   deactivating the first pair of the power switching elements to generate a radio frequency waveform including at least one pulse having an overshoot peak; and
   activating a clipper circuit coupled to the power converter and the power supply to generate a clipping voltage to clip the overshoot peak.

14. The method according to claim 13, further comprising:
   deactivating at least one power switching element of the second pair of the power switching elements.

15. The method according to claim 13, wherein activating the clipper circuit includes:
   increasing voltage at a clipper inductor of the clipper circuit.

16. The method according to claim 15, wherein activating the clipper circuit further includes:
   clamping current at the clipper inductor by a clipper catch diode of the clipper circuit.

17. The method according to claim 16, wherein activating the clipper circuit further includes:
   charging a clipper capacitor of the clipper circuit.

18. The method according to claim 17, wherein activating the clipper circuit further includes:
   controlling at least one clipper switching element of the clipper circuit to maintain the clipping voltage at the clipper capacitor.

* * * * *